US010675475B2

(12) United States Patent
Rao et al.

(10) Patent No.: US 10,675,475 B2
(45) Date of Patent: Jun. 9, 2020

(54) NETWORKING OF IMPLANTABLE MEDICAL DEVICES AND WEARABLE DEVICES

(71) Applicants: IP Holdings, Inc., Palo Alto, CA (US); Rekha K. Rao, Palo Alto, CA (US)

(72) Inventors: Raman K. Rao, Palo Alto, CA (US); Sanjay K. Rao, Palo Alto, CA (US)

( * ) Notice: Subject to any disclaimer, the term of this patent is extended or adjusted under 35 U.S.C. 154(b) by 0 days.

(21) Appl. No.: 15/206,130

(22) Filed: Jul. 8, 2016

(65) Prior Publication Data
US 2016/0317822 A1    Nov. 3, 2016

Related U.S. Application Data

(63) Continuation of application No. 14/253,142, filed on Apr. 15, 2014, now Pat. No. 9,561,381, which is a
(Continued)

(51) Int. Cl.
| | | |
|---|---|---|
| A61N 1/08 | (2006.01) |
| A61N 1/372 | (2006.01) |
| G06F 19/00 | (2018.01) |
| A61B 5/00 | (2006.01) |
| H04L 29/06 | (2006.01) |
| A61B 5/026 | (2006.01) |
| A61B 5/1455 | (2006.01) |
| A61N 1/362 | (2006.01) |
| A61N 1/365 | (2006.01) |
| A61N 1/39 | (2006.01) |
| H04B 13/00 | (2006.01) |
| A61N 1/36 | (2006.01) |
| A61N 1/37 | (2006.01) |
| H04M 11/04 | (2006.01) |

(52) U.S. Cl.
CPC ........ *A61N 1/37264* (2013.01); *A61B 5/0015* (2013.01); *A61B 5/0022* (2013.01); *A61B 5/0031* (2013.01); *A61B 5/026* (2013.01); *A61B 5/14551* (2013.01); *A61N 1/362* (2013.01); *A61N 1/365* (2013.01); *A61N 1/36007* (2013.01); *A61N 1/37* (2013.01); *A61N 1/372* (2013.01); *A61N 1/37211* (2013.01); *A61N 1/37217* (2013.01); *A61N 1/37288* (2013.01); *A61N 1/39* (2013.01); *A61N 1/3956* (2013.01); *G06F 19/34* (2013.01); *G06F 19/3418* (2013.01); *H04B 13/005* (2013.01); *H04L 63/0861* (2013.01); *H04M 11/04* (2013.01)

(58) Field of Classification Search
CPC .... A61N 1/372; A61N 1/37288; G06F 19/34; G06F 19/3418; A61B 5/0002; A61B 5/0031
See application file for complete search history.

(56) References Cited

U.S. PATENT DOCUMENTS

| 4,117,542 A | 9/1978 | Klausner et al. |
|---|---|---|
| 4,386,412 A | 5/1983 | Ito |

(Continued)

FOREIGN PATENT DOCUMENTS

| EP | 0849925 A1 | 6/1998 |
|---|---|---|
| WO | WO 1992/003884 | 3/1992 |

*Primary Examiner* — Andrew W Bee

(57) ABSTRACT

A system level scheme for networking of implantable devices, electronic patch devices/sensors coupled to the body, and wearable sensors/devices with cellular telephone/mobile devices, peripheral devices and remote servers is described.

16 Claims, 6 Drawing Sheets

Related U.S. Application Data continuation of application No. 14/092,367, filed on Nov. 27, 2013, now Pat. No. 8,736,441, which is a continuation of application No. 13/665,065, filed on Oct. 31, 2012, now Pat. No. 8,653,966, which is a continuation of application No. 13/432,873, filed on Mar. 28, 2012, now Pat. No. 8,325,031, which is a continuation of application No. 11/805,610, filed on May 23, 2007, now Pat. No. 8,183,998.

(56) References Cited

U.S. PATENT DOCUMENTS

| | | | |
|---|---|---|---|
| 4,465,401 A | 8/1984 | Stoddard et al. | |
| 4,514,920 A | 5/1985 | Shafrir et al. | |
| 4,517,660 A | 5/1985 | Fushimoto et al. | |
| 4,670,747 A | 6/1987 | Barras et al. | |
| 4,675,653 A | 6/1987 | Priestly | |
| 4,696,054 A | 9/1987 | Tsugei et al. | |
| 4,719,338 A | 1/1988 | Avery et al. | |
| 4,772,876 A | 9/1988 | Laud | |
| 4,844,637 A | 7/1989 | Buisson et al. | |
| 4,853,884 A | 8/1989 | Lata et al. | |
| 4,908,866 A | 3/1990 | Goldwasser et al. | |
| 4,912,640 A | 3/1990 | Tsugei | |
| 5,034,858 A | 7/1991 | Kawamoto et al. | |
| 5,164,723 A | 11/1992 | Nebenzahi | |
| 5,195,130 A | 3/1993 | Weiss et al. | |
| 5,198,798 A * | 3/1993 | Lietzow | B60Q 1/305 340/12.22 |
| 5,263,118 A | 11/1993 | Cornelison | |
| 5,276,794 A | 1/1994 | Lamb, Jr. | |
| 5,335,276 A | 8/1994 | Thompson et al. | |
| 5,351,189 A | 9/1994 | Doi et al. | |
| 5,379,341 A | 1/1995 | Wan | |
| 5,396,443 A | 3/1995 | Mese et al. | |
| 5,410,738 A | 4/1995 | Diepstraten et al. | |
| 5,440,502 A | 8/1995 | Register | |
| 5,465,401 A | 11/1995 | Thompson | |
| 5,496,992 A | 3/1996 | Madan et al. | |
| 5,502,460 A | 3/1996 | Bowen | |
| 5,513,242 A | 4/1996 | Mukerjee et al. | |
| 5,517,553 A | 5/1996 | Sato | |
| 5,539,391 A | 7/1996 | Yuen | |
| 5,552,806 A | 9/1996 | Lenchik | |
| 5,555,258 A | 9/1996 | Snelling et al. | |
| 5,559,794 A | 9/1996 | Willis et al. | |
| D374,675 S | 10/1996 | Sakai et al. | |
| 5,561,446 A | 10/1996 | Montlick | |
| 5,565,929 A | 10/1996 | Tanaka | |
| 5,566,205 A | 10/1996 | Delfine | |
| 5,572,576 A | 11/1996 | Klausner et al. | |
| 5,577,118 A | 11/1996 | Sasaki et al. | |
| 5,594,953 A | 1/1997 | Ross et al. | |
| 5,604,688 A | 2/1997 | Chu et al. | |
| 5,615,277 A | 3/1997 | Hoffman | |
| 5,644,338 A | 7/1997 | Bowen | |
| 5,660,246 A | 8/1997 | Kaman | |
| 5,673,080 A | 9/1997 | Biggs et al. | |
| 5,751,835 A | 5/1998 | Topping et al. | |
| 5,760,773 A | 6/1998 | Berman et al. | |
| 5,784,888 A | 7/1998 | Termuehlen | |
| 5,793,413 A | 8/1998 | Hylton et al. | |
| 5,793,639 A | 8/1998 | Yamazaki | |
| 5,797,089 A | 8/1998 | Nguyen | |
| 5,847,698 A | 12/1998 | Reavey et al. | |
| 5,854,997 A | 12/1998 | Sukeda et al. | |
| 5,856,819 A | 1/1999 | Vossler | |
| 5,878,399 A | 3/1999 | Peralta | |
| 5,901,222 A | 5/1999 | Macor | |
| 6,046,730 A | 4/2000 | Bowen et al. | |
| 6,058,304 A | 5/2000 | Callaghan et al. | |
| 6,121,960 A | 9/2000 | Carroll et al. | |
| 6,141,592 A * | 10/2000 | Pauly | A61N 1/37223 607/60 |
| 6,209,034 B1 | 3/2001 | Gladwin et al. | |
| 6,268,806 B1 | 7/2001 | Frager et al. | |
| 6,295,052 B1 | 9/2001 | Kato et al. | |
| 6,358,202 B1 * | 3/2002 | Arent | A61N 1/37282 128/920 |
| 6,440,069 B1 | 8/2002 | Raymond et al. | |
| 6,440,502 B1 | 8/2002 | Lee | |
| 6,525,750 B1 | 2/2003 | Knox | |
| 6,587,700 B1 | 7/2003 | Meins et al. | |
| 6,751,473 B1 | 6/2004 | Goyal et al. | |
| 6,858,006 B2 * | 2/2005 | MacCarter | A61B 5/0002 128/903 |
| 6,882,859 B1 | 4/2005 | Rao et al. | |
| 6,920,283 B2 * | 7/2005 | Goldstein | G03B 17/00 396/263 |
| 6,924,773 B1 * | 8/2005 | Paratte | H01Q 7/04 343/728 |
| 7,009,511 B2 * | 3/2006 | Mazar | A61B 5/0031 340/531 |
| 7,044,911 B2 * | 5/2006 | Drinan | A61B 5/14539 128/903 |
| 7,107,547 B2 | 9/2006 | Cule et al. | |
| 7,260,436 B2 * | 8/2007 | Kilgore | A61N 1/36003 607/2 |
| 7,382,247 B2 * | 6/2008 | Welch | A61B 5/0024 340/539.1 |
| 7,629,881 B2 * | 12/2009 | Gao | A61B 5/0002 340/539.12 |
| 8,183,998 B2 | 5/2012 | Rao | |
| 8,325,031 B1 | 12/2012 | Rao | |
| 8,653,966 B2 | 2/2014 | Rao | |
| 8,736,441 B2 | 5/2014 | Rao | |
| 9,561,381 B2 | 2/2017 | Rao | |
| 2002/0072860 A1 * | 6/2002 | Amano | A61B 5/02007 702/19 |
| 2002/0123673 A1 * | 9/2002 | Webb | G06F 19/3418 600/300 |
| 2003/0041032 A1 | 2/2003 | Ballin et al. | |
| 2003/0112148 A1 * | 6/2003 | Belliveau | H04L 12/403 340/12.22 |
| 2004/0003256 A1 * | 1/2004 | Coffy | G06Q 20/3674 713/179 |
| 2004/0049245 A1 * | 3/2004 | Gass | A61N 1/37235 607/60 |
| 2005/0146431 A1 | 7/2005 | Hastings et al. | |
| 2005/0182389 A1 | 8/2005 | LaPorte et al. | |
| 2006/0034252 A1 * | 2/2006 | Karaoguz | H04W 40/08 370/351 |
| 2006/0052945 A1 * | 3/2006 | Rabinowitz | G06F 19/24 702/20 |
| 2006/0064143 A1 * | 3/2006 | Von Arx | A61B 5/0031 607/60 |
| 2006/0075014 A1 * | 4/2006 | Tharappel | H04L 63/0428 709/202 |
| 2006/0173498 A1 * | 8/2006 | Banville | A61N 1/39 607/5 |
| 2006/0222179 A1 | 10/2006 | Jensen et al. | |
| 2007/0100660 A1 * | 5/2007 | Carosso | G06F 19/327 705/2 |
| 2007/0103324 A1 * | 5/2007 | Kosuge | E03F 7/00 340/618 |
| 2007/0191070 A1 | 8/2007 | Rao | |
| 2008/0046038 A1 * | 2/2008 | Hill | A61B 5/0031 607/60 |
| 2008/0048960 A1 | 2/2008 | Jacobsen et al. | |
| 2008/0146272 A1 | 6/2008 | Rao et al. | |
| 2008/1029465 | 6/2008 | Rao | |
| 2008/0164979 A1 * | 7/2008 | Otto | A61B 5/0002 340/286.01 |
| 2008/0167614 A1 * | 7/2008 | Tolkowsky | A61M 16/00 604/131 |
| 2008/0191866 A1 * | 8/2008 | Falck | A61B 5/0006 340/539.12 |

(56) References Cited

U.S. PATENT DOCUMENTS

2008/0200779 A1* 8/2008 Zimmerling ....... A61N 1/36032
                                                    600/309
2011/0059777 A1    3/2011 Rao

* cited by examiner

MATRIX FOR DYNAMIC CONFIGURATION OF NEW FUNCTIONAL NETWORKS

| DEFINED NETWORKS | DEVICES | | | | | |
|---|---|---|---|---|---|---|
| Implant Device Network | ID1 | ID2 | ID3 | ID4 | ID5 | ID6 |
| Electronic Patch Device Network | EPD1 | EPD2 | EPD3 | EPD4 | EPD5 | EPD6 |
| Wearable Device Network | WD1 | WD2 | WD3 | WD4 | WD5 | WD6 |
| LAN / WAN / INTERNET Home Network / Office Network Health Care Facility Network Transportation Network Public Access Network | CT | MD | PHMA | PC / TV | SERVER | PRINTER |

FIG. 6

NETWORKING OF IMPLANTABLE MEDICAL DEVICES AND WEARABLE DEVICES

CROSS-REFERENCE TO RELATED APPLICATIONS

The present application is a continuation of U.S. patent application Ser. No. 14/253,142 filed Apr. 15, 2014, which is a continuation of U.S. patent application Ser. No. 14/092,367 filed Nov. 27, 2013 (now U.S. Pat. No. 8,736,441 issued May 27, 2014), which is a continuation of U.S. patent application Ser. No. 13/665,065 filed Oct. 31, 2012 (now U.S. Pat. No. 8,653,966 issued Feb. 18, 2014), which is a continuation of U.S. patent application Ser. No. 13/432,873 filed Mar. 28, 2012 (now U.S. Pat. No. 8,325,031 issued Dec. 4, 2012), which is a continuation of U.S. patent application Ser. No. 11/805,610 filed May 23, 2007 (now U.S. Pat. No. 8,183,998 issued May 22, 2012), each of which is incorporated by reference in its entirety.

ABBREVIATIONS

Cellular Telephone is abbreviated as CT.
Mobile Device is abbreviated as MD.
Mobile Health Appliance is abbreviated as MHA.
Intelligent Personal Health Management Appliance is abbreviated as IPHMA.
Personal Health Management is abbreviated as PHM.
Implantable Device is abbreviated as ID.
Electro-Physiological/Electronic Patch device is abbreviated as EP wherein said device is configured for attachment/coupling to the body.
Wearable Device is abbreviated as WD wherein said device is configured for carriage on the body including in garments/clothing and various other forms of carriage.
The electro-physiological device/electronic patch device/biological sensor device are referred to as EP device for convenience.
The terms Electro-Physiological Device/Electronic Patch Device/Biological Sensor include devices that sense, measure, monitor, control and manage various types of human/animal biological and bodily parameters in one or more forms and functions.

BACKGROUND

The present application additionally cross references and incorporates by reference related co-pending U.S. patent application Ser. No. 11/001,668 filed Nov. 30, 2004.

The present application further cross references and incorporates by reference the U.S. patent application Ser. No. 11/018,862 filed Dec. 19, 2004 which is a continuation in part of U.S. patent application Ser. No. 11/001,668 filed Nov. 30, 2004.

In the cross referenced applications, Rao et al., the common inventor of the present disclosure, teaches a system level scheme and method for the networking of various types of devices including mobile devices having capability for communication, command and control of voice and data information and the networking of intelligent appliances, peripheral devices and sensors with a central server/network server comprising said wired or wireless network.

Additionally, Rao et al., in the cross referenced applications, teach the unique identification of said devices and the encryption/decryption of communications for secure and intended access to a selected device forming a communication network. Further Rao et al teach the communication of information over a plurality of communication channels wherein said communication channels may be configured for one or more communication protocols/methods including the multiplexing of a selected communication channel from a first communication to a second communication protocol/method. Rao et al further teach the feature wherein a mobile device may be configured with a web server capability to perform the additional functions of a server.

Further, Rao et al., in the cross referenced applications, teach novel methods for utilizing the mobile device for tracking and managing health information including gastronomic information, physical activity and other parameters. Additionally, Rao et al in cross referenced applications teach the use of novel electronic patch device/activated electronic patch device/drug delivery device/pain management device and biological sensors that are configured for affixing/coupling to the body and carriage on the body including a number of novel personal health management appliances.

There is a need for systems and methods for the wired and wireless networking of medical devices ranging from implantable medical devices, electronic patch devices that are configured for directly affixing/coupling to the body and wearable devices that are configured for carriage on the body. Additionally there is a need for devices that may be used for identification and authentication of the person and for controlling the access to one or more devices and one or more networks comprising of said devices.

The prior art of record does not teach the means for real time networking among a plurality of implantable medical devices implanted and present within the body. Consequently, there is a need for wired and wireless networking of one or more implanted medical devices within the body; and further a need for system and methods for connecting one or more of said implanted devices and the implantable device network to one or more networks external to the body. In addition there is a need for an implantable device for performing the functions of a server and alternately the configuration of at least one implantable medical device configured for performing the additional functions of a server.

The prior art of record further does not teach the means for real time networking among a plurality of electronic patch devices and other types of electro-physiological/biological sensors that are affixed/coupled directly to the body. Consequently, there is a need for the wired and wireless networking of electronic patch devices and other types of electro-physiological/biological sensors that are affixed/coupled to the body; and further there is a need for systems and methods for connecting one or more of said electronic patch devices and other types of electro-physiological/biological sensors and the connection of the network forming said devices to one or more networks that are located internal to the body, affixed/coupled to the body and externally remote to the body. In addition there is a need for the novel use of an electronic patch device/biological sensor device for performing the functions of a server and alternately the configuration wherein at least one electronic patch device/biological sensor device is configured for performing the additional functions of a server.

The prior art of record further does not teach the means for real time networking among a plurality of wearable devices and other types of devices that are configured for carriage on the body. Thus, there is a need for wired and wireless networking of wearable devices and other types of devices that are configured for carriage on the body. Furthermore, there is a need for systems and methods for connecting one or more of said devices and the connection of the network forming said devices to one or more networks that are located internal to the body, affixed/coupled to the body and externally remote to the body. In addition there is a need for wearable devices and other types of devices that are configured for carriage on the body for performing the functions of a server; and alternately the configuration wherein at least one wearable devices and other types of devices that are configured for carriage on the body is configured for performing the additional functions of a server.

The prior art does not teach the seamless and secure networking among the devices forming the three different networks described above and further does not teach the seamless and secure coupling of each of said networks with each other to enable the utility of delivering novel health care applications for sensing, measuring, monitoring, managing and controlling the desired parameters affecting a person internal of the body, on the body and external of the body. There is a need for configuring the body with all three types of networks described above. As the number of implantable devices, electronic patch devices/other types of biological sensors that are affixed/coupled to the body and the wearable devices configured for carriage on the body proliferate, there is a need for defining a system level architecture and methods for configuring the different types of networks and for seamlessly enabling communication between the various networks forming said life enhancing/supporting functions related to a person's health. Additionally, there is a need for uniquely identifying said devices and for authenticating the communication between said devices; and also the persons accessing said devices to ensure that spurious signals, accidental access or unauthorized access is precluded.

In the prior art various types of devices lacked the multi channel communication capability and also the capability of a single device to perform multiple functions such as measuring temperature, blood flow, blood oxygen level, heart pacing functions, measuring electro cardio gram, ECG signals and other functions. Consequently, there is a need for multifunction implantable devices, electro-physiological devices, electronic patch devices, biological sensors and wearable devices and the system for networking said multifunction devices to dynamically form a plurality of networks for measuring, monitoring, managing, communication, command and control of a selected biological parameter and biological information at a selected time and in a selected manner.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

SUMMARY

The present invention teaches novel systems and methods for networking of implantable devices, devices configured for electro-physiological information, biological sensors, devices configured affixing/coupling to a body and wearable devices for carriage on a body. The present invention additionally teaches the methods for the sensors and devices to be configurable with at least one unique identification number whereby the devices and sensors may be accessed, communicated with and addressed with specificity, security and safety in one or more networks formed by said devices and sensors. The system for addressing a device and or a sensor by a unique identification number is not taught in the prior art of record. Additionally, the device and/or the sensor may be configured with a unique device/sensor profile. The user may be described and configured with a user profile comprising of user information including health information such that the user information/profiles and the device/sensor information/profiles may be used individually or in tandem with each other. These novel features are not taught in the prior art of record. The various networks comprising the medical devices are configured for real time data acquisition, for communication of biological information, for archiving said data for contemporaneous utility or for utility at a selected time, for analyzing said data, for determining trends, for communication of said data to one or more health professionals and for comprehensive real time management of the personal health of an individual in a cost effective manner in accordance with the quality/cost objectives that are acceptable to the individual and society.

The present invention teaches novel systems, methods and devices to solve the above enumerated problems not addressed in the prior art. Various other important objectives of the present invention are also enumerated below. Other objectives may become apparent to those knowledgeable in the art and the invention is not to be construed as limited to the specific objectives enumerated herein:

A. System level scheme for networking of implantable devices located within a human or mammalian body:

1. An objective of the present invention is the networking of one or more implantable devices located within a body for communication, coordination, command and control of functions performed by said implantable devices.

2. An objective of the present invention is to identify an individual and an implantable device associated with said individual by a plurality of means for secure and seamless networking.

3. Another objective is to uniquely identify the individual by speech/voice recognition, photo, finger print and other biometric identification methods to ensure that the health information acquired/accessed from an implantable device is uniquely and securely related to the specific individual in real time for safety and accurate personal health management.

4. Another objective of the present invention is to enable the individual to set permission levels for access to the implantable device by means of a secure server such as an escrow server and other means.

5. Another objective of the present invention is to enable access to the implantable device via one or more of the biometric authentication methods and one or more of the selected I/O methods.

6. Another objective of the present invention is to configure the implantable devices and the network formed by said implantable devices for authenticated communication of information.

7. Another objective of the present invention is to enable seamless and secure communication of information among one or more of the implantable devices within an implant device network.

8. Another objective of the present invention is to enable seamless and secure communication of information between one or more of the implantable devices within an implant device network and one or more of the devices located external to the body and the external networks.

9. Another objective of the present invention is a multi-channel implantable device configured for communication of information on one or more input and out put channels.

10. Another objective of the present invention is a multi-channel implantable device configured for communication of information on one or more input and out put channels that are multiplexed.

11. Another objective of the present invention is a multi-function implantable device configured for communication of information on one or more input and out put channels.

12. Another objective of the present invention is a multi-function implant device configured for communication of information on one or more input and out put channels wherein the function, power level, frequency and other parameters of the device are configurable from a first configuration to a different second configuration by software selection.

B. System level scheme for networking of devices affixed/attached/coupled to a human or mammalian body:

13. An objective of the present invention is the networking of one or more devices electrophysiological/electronic patch/biological sensor devices coupled to a body to enable enhanced communication, coordination, command and control of functions performed by said devices.

14. An objective of the present invention is to identify an individual and a electrophysiological/electronic patch/biological sensor device coupled to said individual by a plurality of means for secure and seamless networking.

15. Another objective is to uniquely identify the individual by speech/voice recognition, photo, finger print and other biometric identification methods to ensure that the health information acquired/accessed from a device coupled to the body is uniquely and securely related to the specific individual in real time for safety and accurate personal health management.

16. Another objective of the present invention is to enable the individual to set permission levels for access to the electrophysiological/electronic patch/biological sensor device coupled to the body by means of a secure server such as an escrow server and other means.

17. Another objective of the present invention is to enable access to the electrophysiological/electronic patch/biological sensor device coupled to the body via one or more of the biometric authentication methods and one or more of the selected I/O methods.

18. Another objective of the present invention is to configure the electrophysiological/electronic patch/biological sensor device coupled to the body and the network formed by said electrophysiological/electronic patch/biological sensor devices coupled to the body for authenticated communication of information.

19. Another objective of the present invention is to enable seamless and secure communication of information among one or more of the electrophysiological/electronic patch/biological sensor device coupled to the body within a device network comprising of said electrophysiological/electronic patch/biological sensor device coupled and located on the body.

20. Another objective of the present invention is to enable seamless and secure communication of information between one or more of the electrophysiological/electronic patch/biological sensor device coupled to the body within a device network of electrophysiological/electronic patch/biological sensor device coupled to the body; and one or more of the devices implanted within the body and the implant device network; and one or more of the devices located external to the body and the external networks.

21. Another objective of the present invention is a multi-channel electrophysiological/electronic patch/biological sensor device configured for communication of information on one or more input and out put channels.

22. Another objective of the present invention is a multi-channel electrophysiological/electronic patch/biological sensor device configured for communication of information on one or more input and out put channels that are multiplexed.

23. Another objective of the present invention is a multi-function electrophysiological/electronic patch/biological sensor device configured for communication of information on one or more input and out put channels.

24. Another objective of the present invention is a multi-function electrophysiological/electronic patch/biological sensor device configured for communication of information on one or more input and out put channels wherein the function, power level, frequency and other parameters of the device are configurable from a first configuration to a different second configuration by software selection.

C. System level scheme for networking of wearable devices for carriage on a human or mammalian body:

25. An objective of the present invention is the networking of one or more wearable devices for carriage on a body to enable enhanced communication, coordination, command and control of functions performed by said devices.

26. An objective of the present invention is to identify an individual and a wearable device carried by said individual by a plurality of means for secure and seamless networking.

27. Another objective is to uniquely identify the individual by speech/voice recognition, photo, finger print and other biometric identification methods to ensure that the health information acquired/accessed from a wearable device is uniquely and securely related to the specific individual in real time for safety and accurate personal health management.

28. Another objective of the present invention is to enable the individual to set permission levels for access to a wearable device by means of a secure server such as an escrow server and other means.

29. Another objective of the present invention is to enable access to a wearable device via one or more of the biometric authentication methods and one or more of the selected I/O methods.

30. Another objective of the present invention is to configure the wearable device and the network formed by said wearable devices for authenticated communication of information.

31. Another objective of the present invention is to enable seamless and secure communication of information among one or more of the wearable devices and the device network comprising of said wearable devices.

32. Another objective of the present invention is to enable seamless and secure communication of information between one or more of the wearable devices and a device network of wearable devices; and one or more of the electrophysiological/electronic patch/biological sensor devices coupled to the body and the network formed by said electrophysiological/electronic patch/biological sensor devices coupled to the body; and one or more of the devices implanted within the body and the implant device network; and one or more of the devices located external to the body and the external networks.

33. Another objective of the present invention is to dynamically configure a selected functional network of devices by selecting one or more devices across the implant device network, the electrophysiological/electronic patch/ biological sensor device network, the wearable device network and one or more of the external networks wherein the dynamically configured network of devices executes selected functional tasks.

34. Another objective of the present invention is a multi-function wearable device configured for communication of information on one or more input and out put channels wherein the function, power level, frequency and other parameters of the device are configurable from a first configuration to a different second configuration by software selection.

Other objects, features and advantages of the present invention will become apparent from the following detailed description when taken in conjunction with the accompanying drawings.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 2 also shows an external view of a body of a person/mammal with one or more electronic patch/electro-physiological/biological sensor devices located on/affixed to/coupled to the body and the second network formed by said devices that are coupled to the body. FIG. 2 further shows the connectivity of said first network and the second network to one or more external networks including a home network, a local area network, LAN, a wide area network, WAN, an office network, a factory network, a health care network, a transportation network, a public access network and the Internet by wired or wireless communication means.

FIG. 3 also shows an external view of a body of a person/mammal with one or more electronic patch/electro-physiological/biological sensor devices located on/affixed to/coupled to the body and the second network formed by said devices that are coupled to the body.

FIG. 3 further shows the connectivity of said first network, the second network and the third network to one or more external networks including a home network, a local area network, LAN, a wide area network, WAN, an office network, a factory network, a health care network, a transportation network, a public access network and the Internet by wired or wireless communication means.

FIG. 4 shows an illustrative functional block diagram configuration of an implantable device; an electronic patch/electro-physiological/biological sensor device that may be located on, affixed to or coupled to the body; and a wearable device for carriage on the body wherein the illustrated block diagram illustration of these different devices is intended to show multiple input and output channels for one or more of wired and wireless communication. The block diagram configuration shown is for illustrative purposes and is not intended to be limiting in any way as to the presence of one or more of the functional block and the exclusion of one or more of the functional blocks. As an example an antenna is not shown in the illustration but those knowledgeable in the art would realize that for wireless transmission an antenna is intended.

FIG. 6 shows a matrix organization of the different types of defined networks on the vertical, Y axis and different types of devices that are available within each of these defined networks on the horizontal X axis. The matrix organization is for illustrative purposes only and is intended to show that any number of devices may be selected from a selected network and coupled to one or more devices from one or more other defined networks to dynamically configure to form a new/another network of devices spanning across these selected networks.

DETAILED DESCRIPTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 1:
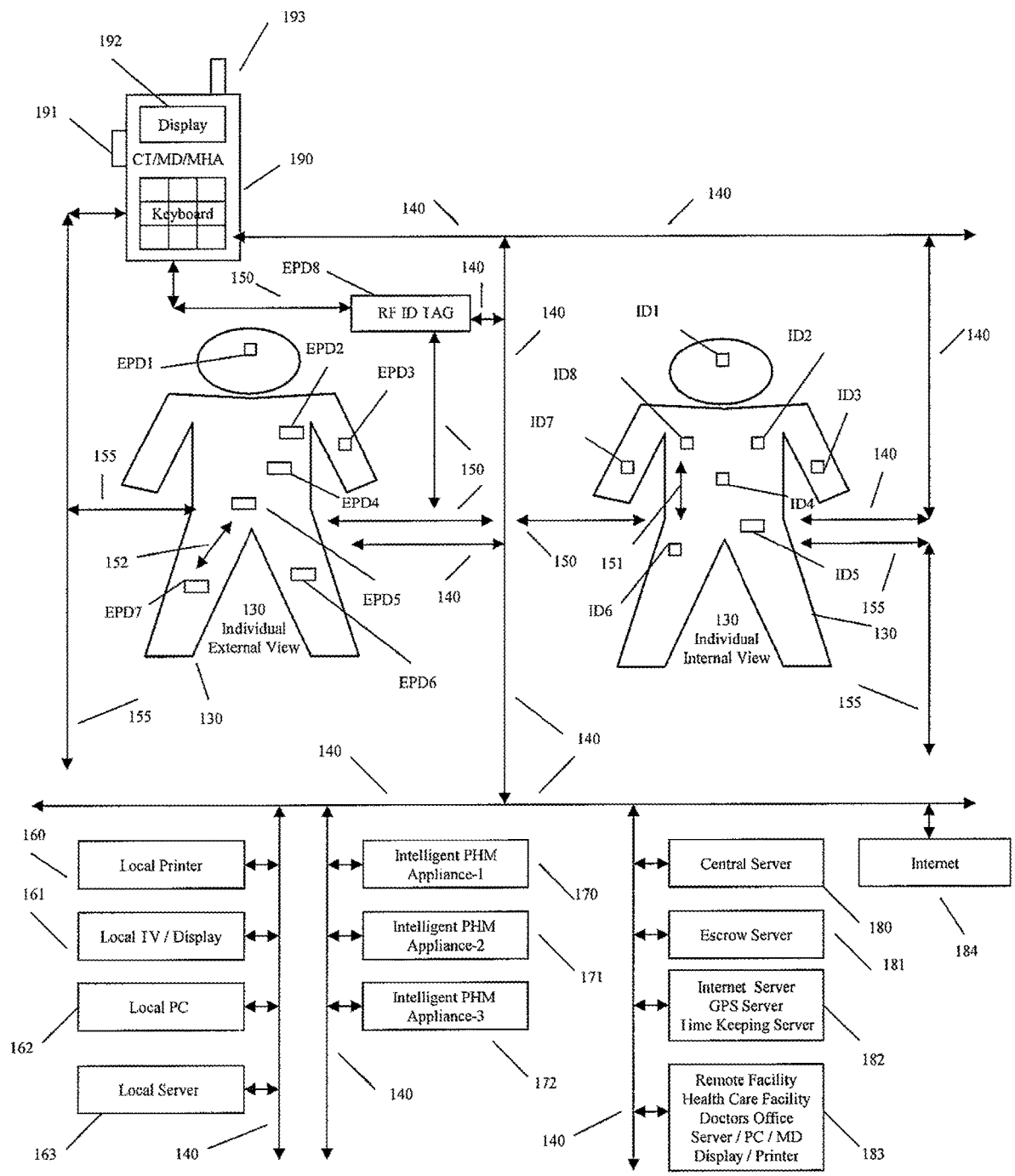
FIG. 1 shows an internal view of a body of a person/mammal and an external view of a body of a person/mammal with one or more devices located internal to the body, with one or more devices located on/affixed to/coupled to the body and one or more devices located external to the body wherein said devices form a plurality of wired and wireless networks for the acquisition, processing, computation, storage and communication of information; and further enable the command and control of said individual devices and the plurality of networks comprising of said devices.

The novel embodiments and teachings of the present invention will be made clear in conjunction with the figures and the descriptions:

FIG. 1 shows a system level architecture for wired or wireless networking of implantable devices located within the body, electronic patch devices/biological sensors affixed/coupled to the surface of the body and a plurality of devices located external to the body. The system level architecture and the various wired and wireless networks formed by the various devices are made clear by referring in detail to FIG. 1 and examining the detailed description of the figure section by individual section:

1. Communication paths of implant devices internal to and external of the body:

FIG. 1 shows an internal and external view of a body of an individual 130.

FIG. 1 shows an internal view of the human body, 130 showing a number of implant devices, ID1, ID2, ID3, ID4, ID5, ID6, ID7 and ID8 located at a plurality of locations within the body. As an example ID2 may perform the functions of a heart pacemaker, ID6 may perform the functions of a gastric pacemaker, ID5 may simply perform the functions of a server and ID8 may perform the functions of an implantable radio frequency identification device, RFID that uniquely identifies the individual 130 and stores selected information related to the individual 130. One or more of the other implant devices may perform various assigned functions and are shown for illustration purposes to indicate that a plurality of implant devices that may exist within the body to measure, monitor and control the selected bodily function of the individual 130.

1.1 In one preferred embodiment, the communication path between a first implant device and a plurality of other implant devices is represented by 151 wherein the communication path 151 located internal to the body represents a wired or wireless communication path utilizing a selected communication protocol best suited for secure communication between one or more implant devices. As an example the communication path 151 may be optimized and configured for minimizing power consumption and limiting communication interference with external devices. The communication path 151 may similarly be optimized based on a number of other considerations.

1.2 In one preferred embodiment, a wireless communication path between one or more of the implant devices and the outside world is represented by the wired or wireless communication path 155 wherein communication path 155 may utilize same or different communication protocols as communication path 151. As an example the communication path 155 may be optimized and configured for minimizing power consumption and to ensure secure communication with external devices. The communication path 155 may similarly be optimized based on a number of other considerations.

1.3 In another preferred novel embodiment, one or more implant devices may be configured to communicate using communication path 151, with a selected implant device such as ID5 configured to perform the additional function of a server wherein said server configured implant device enables the communication between one or more implant devices and one or more devices/networks located external of the body via the communication path 155.

1.4 In another preferred novel embodiment a dedicated server device such as ID5, may be implanted within the body to solely perform server functions with the ability to control communication of information through the implanted server device ID5 via an internal communication path 151 and an external communication path 155.

1.5 In another preferred embodiment a dedicated server device such as ID5, may be implanted within the body to solely perform server functions with the ability to control communication of information through the implanted server device ID5 via an internal communication path 151 and one or more external communication paths 150, 155 and 140.

1.6 In another preferred embodiment an implant device such as ID1, ID2, ID3, ID4, ID6 and ID7 may be implanted within the body to perform one or more medical device functions wherein one or more of these implant devices may communicate via an internal communication path 151 and a one or more external communication paths 150, 155 and 140. Communication path 140 may be connected to the local area network, LAN, wide area network, WAN and the Internet.

1.6 In another preferred embodiment an implant device located internal to the body may communicate with a proximate mobile device such as a cellular telephone/personal digital assistant/lap top computer, 190 and other stationary and mobile devices located external to the body via the wired or wireless communication path 155 utilizing a selected communication protocol that optimizes the communication between the selected implant device and the selected external proximate communication device.

1.7 In another preferred embodiment an implant device, ID1, ID2, ID3, ID4, ID5, ID6, ID7 and ID8 located internal to the body may communicate with one or more peripheral devices such as a local printer 160, a local TV/display 161, a local personal computer, PC 162, a local server 163, an intelligent personal health management appliance such as a portable cardiac function monitoring appliance, 170; another intelligent personal health management appliance 171; another intelligent personal health management appliance 172, a central server 180, an escrow server 181, an Internet server/global positioning server, GPS/a time keeping server 182 and a remote facility/a health care facility/a doctors office 183; and a local server 163, a local PC 162, a mobile device CT/MD/MHA 190 configured with a display 192, an external port 191, an antenna 193 and a keyboard via one or more wired or wireless communication paths 140 and 155 utilizing a selected communication protocol that optimizes the communication between the selected implant device and the selected external peripheral device.

1.8 In another preferred embodiment an implant device, ID1, ID2, ID3, ID4, ID5, ID6, ID7 and ID8 located internal to the body may communicate with one or more electronic patch devices/biological sensor devices, EPD devices that are coupled to the body at one or more locations on the body via the wired and wireless communication path 150. The communication path 150 is optimized for proximate communication between one or more implant devices located internal of the body and one or more of the EPD devices, EPD1, EPD2, EPD3, EPD4, EPD5, EPD6, EPD7 and EPD8 coupled to the external surface of the body, 130. The communication paths 155 and 140 while useful for communication may not be best suited for the selected communication as these paths may be better configured for distant communication with devices that are not as proximate such as one or more of the remote devices, for example 170 and the Internet.

1.9 In another preferred embodiment an implant device ID1, ID2, ID3, ID4, ID5, ID6, ID7 and ID8 located internal to the body may communicate with one or more mobile devices, 190 via the communication path 155 wherein the communication path 155 is optimized for proximate communication using a selected communication protocol best suited for proximate communication. Alternately, an implant device ID1, ID2, ID3, ID4, ID5, ID6, ID7 and ID8 located internal to the body may communicate with one or more mobile devices, 190 via the communication path 140 wherein the communication path 140 is optimized for distant communication using a selected communication protocol best suited for distant communication with peripheral devices and the Internet. Communication path 140 may be connected to the local area network, LAN, wide area network, WAN and the Internet, 184.

Referring once again to FIG. 1 and particularly the external view of a body of the individual 130:

2. Communication paths of electronic patch device/biological sensor device, EPD devices coupled to the body:

2.1 In another preferred embodiment an electronic patch devices/biological sensor devices, EPD device EPD1, EPD2, EPD3, EPD4, EPD5, EPD6, EPD7 and EPD8 coupled to the body may communicate with one or more implant devices, ID1, ID2, ID3, ID4, ID5, ID6, ID7 and ID8 located internal to the body via the wired and wireless communication path 150. The communication path 150 may be optimized for proximate communication between one or more of the EPD devices, EPD1, EPD2, EPD3, EPD4, EPD5, EPD6, EPD7 and EPD8 that are coupled to the external surface of the body and one or more of the implant devices, ID1, ID2, ID3, ID4, ID5, ID6, ID7 and ID8 located internal to the body. The communication paths 155 and 140 while useful for communication may not be best suited for the selected communication as these communication paths/communication protocols are better configured for distant communication with devices that are not as proximate.

2.2 In another preferred embodiment an electronic patch devices/biological sensor devices, EPD device EPD1, EPD2, EPD3, EPD4, EPD5, EPD6, EPD7 and EPD8 coupled to the body may communicate with one or more peripheral devices such as a local printer 160, a local TV/display 161, a local personal computer, PC 162, a local server 163, an intelligent personal health management appliance such as a portable cardiac function monitoring appliance, 170; another intelligent personal health management appliance 171; another intelligent personal health management appliance 172, a central server 180, an escrow server 181, an Internet server/global positioning server, GPS/a time keeping server 182 and a remote facility/a health care facility/a doctors office 183; and another server/PC/MD/display/printer located remotely via one or more wired or wireless communication paths 140 and 155 utilizing a selected communication protocol that optimizes the communication between the selected EPD device and the selected external peripheral device.

2.3 In another preferred embodiment an electronic patch devices/biological sensor devices, EPD device EPD1, EPD2, EPD3, EPD4, EPD5, EPD6, EPD7 and EPD8 coupled to the body may communicate with one or more mobile devices, 190 via the communication path 155 wherein the communication path 155 is optimized for proximate communication using a selected communication protocol best suited for proximate communication. Alternately, EPD device EPD1, EPD2, EPD3, EPD4, EPD5, EPD6, EPD7 and EPD8 coupled to the body may communicate with one or more mobile devices, 190 via the communication path 140 wherein the communication path 140 is optimized for distant communication using a selected communication protocol best suited for distant communication with peripheral devices and the Internet, 184. Communication path 140 may be connected to the local area network, LAN, wide area network, WAN and the Internet, 184.

The invention is further illustrated by the following examples in conjunction with the FIG. 1 and the description:

Implanted medical devices generally are designed to operate at low power in order to conserve battery power and extend the battery life for many years. The replacement of the device/battery is not easily possible since in order to access an implanted device invasive surgical procedures are required. The implant devices are also designed to perform a single function or at best limited and related functions. Range of wireless communication and the communication protocols used are influenced to a large extent by various parameters such as power and the frequency band used for a selected communication. In addition all frequency bands are not either approved or available for communication due to interference and safety considerations. Consequently, communication between an implanted medical device and an external device located in proximity is desirable as such communication may be accomplished with low power and an approved frequency band that minimizes interference. The present invention teaches novel techniques for communication among implanted medical devices and one or more electronic patch devices/biological sensors that are coupled to the external surface of the body.

Example 1

EPD device performing one or more functions of a communication bridge and a gate keeping function to ensure safe, secure and authorized access to an implanted medical device from an external device/network:

The use of hand held devices that perform telemetry functions and communicate with implanted medical devices is known in the prior art. Generally these telemetry devices are used by the trained health care professional/physician to non invasively acquire diagnostic information and to program an implanted medical device. However, the telemetry devices are used in an ad hoc manner and generally they do not provide continuous information.

In the present invention an EPD device, for example EPD1 is attached/coupled externally to the surface of the body on the chest in a location proximate to for example an implanted heart pacemaker, illustrated by ID1 located in the pectoral cavity. EPD1 is configured to communicate with the implanted device ID1 using a first communication protocol. The communication protocol may use a first power level and a first frequency band for communication. The EPD1 device is easily replaceable and may not have the same battery life consideration as the implanted device ID1. Consequently EPD1 is configured for either periodic or continuous communication with one or more implanted devices, such as ID1 using wireless communication path 150 and the communication protocols associated uniquely with the communication path 150. EPD1 may also be configured for either periodic or continuous communication, with one or more and other peripheral devices that are not proximately located in or on the body, for example a remote server 180/a proximate mobile device CT/MD/MHA 190 using one or more communication paths 150, 155 and 140.

Utilizing the above illustrated communication system/architecture, the implanted heart pace maker, ID1 may be polled periodically or continuously by configuring/instructing the EPD1 device by software programming means. The program instructions may be maintained within the memory of the EPD1 device. Alternately the program information may be communicated to the EPD1 device from a proximate device such as a CT/MD/MHA 190 carried by the patient/individual 130. The program instructions may be communicated from a remote device local PC, 163, a remote server 180 and by a doctor using another mobile device at a remote facility 183 using one or more communication paths directly to the EPD1 device or indirectly to the EPD1 device via the CT/MD/MHA 190. The present invention therefore additionally teaches a novel method for continuous telemetry of implanted devices via one or more of a electronic patch device EPD1 or a mobile device CT/MD/MHA 190.

The present invention further enables an implant device, example ID1 to be configured to perform the functions of a server in an implant device network, an electronic patch device example EPD1 to be configured to perform the functions of a server in an electronic patch device network and a mobile device CT/MD/MHA 190 to perform the functions of a server.

There is a need for implanting one or more devices within a body to measure, monitor and control various organ/body functions. The use of implantable heart pace makers, gastric devices, defibrillators and other devices is known. However, the devices are implanted for a specific purpose and generally operate in a standalone manner without adequate consideration being given to the potential need to coordinate the functions performed by a plurality of implant devices acting individually. The human body is an integrated entity and there is a need to look at the human body as an environment similar to a home. The present invention teaches novel method for configuring an implantable device as a server or to perform the additional functions of a server in addition to other intended device functions for sensing, measuring and managing bodily functions.

In the above hierarchical communication architecture and system the implant medical device, ID1 is available for two way communication, command and control of information without unduly draining its battery power which would result from communicating at either a higher power and/or a different communication protocol. This novel communication system/architecture enables the design of small form factor power efficient implant devices without having the complexity associated with dual band communication. In this configuration, the EP device that serves as a bridge between the implant device ID1 and the outside devices/world does the bulk of the transmit/receive functions with the advantage that the battery of the EP device is easily replaceable or alternately the EP device may be discarded when the battery runs out and a replacement EP device used instead.

Additionally, the system and architecture limits the inadvertent or malicious access via a LAN, WAN and the Internet to a life supporting implant device; since the level of access to the implant device is gated and controlled through an intermediate device such as EPD1 and/or through CT/MD/MHA 190. Further level of safety and security is provided as one or more of the EPD device, EPD1 and the CT/MD/MHA, 190 may be configured for executing biometric authentication using one or more of voice, speech, audio, text, hand writing, passwords, user profiles, device profiles, photo, image, video, finger print and retinal scan data related to the individual 130.

Additionally one or more other authorized persons may be authenticated in a similar manner to ensure that only authorized individuals/devices and networks are able to access an implanted device located within the body. This novel invention is of paramount importance as the direct communication and connection of an implanted medical device to the Internet/other unauthorized networks/other unauthorized devices is likely to infect the implant medical device with software viruses and other bugs that impair or disable the functioning of an implanted medical device with the potential for injury to the health and life of the individual. The novel system and architecture of the present invention limits the potential for software related infection of implanted medical devices/systems via the novel hierarchical access approach in conjunction with various types of authentication procedures used singly or in combination for obtaining access to an implanted medical device.

Figure 2:
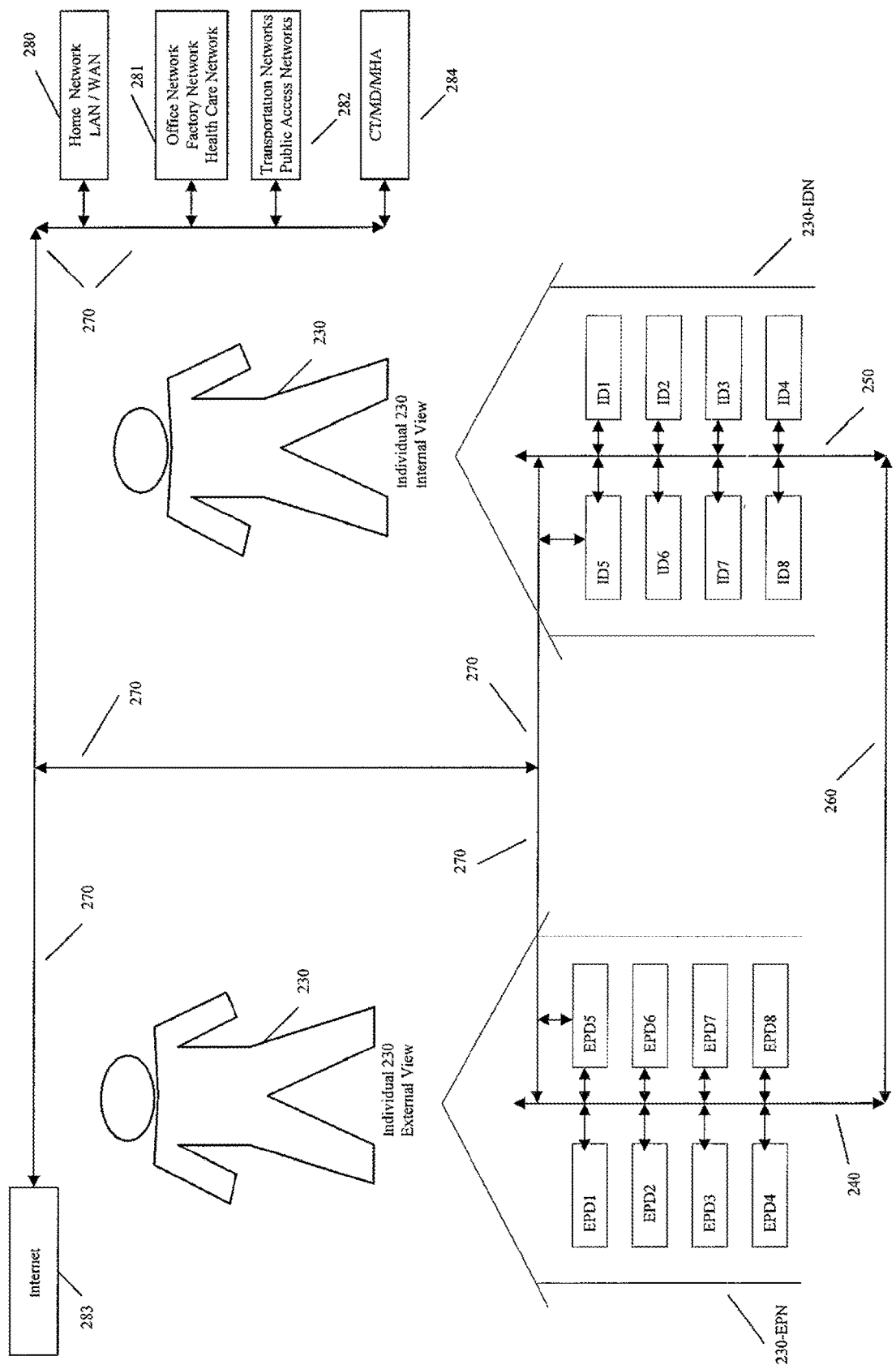
FIG. 2 shows an internal view of a body of a person/mammal with one or more implanted devices located internal to the body and the first implanted device network formed by said implanted devices.

Referring now to FIG. 2 in detail, the figure shows an internal view and an external view of the body of an individual 230.

Looking at detail of the internal view of the individual 230 in FIG. 2, the figure further shows an implant device network labeled with the legend 230-IDN, comprising of a plurality of implanted medical devices ID1, ID2, ID3, ID4, ID5, ID6, ID7 and ID8 that are configured to communicate via wired and wireless communication means. Normally the preferred communication path between one or more of the implanted devices is intended to be a wireless communication path. However, certain selected implanted devices may be connected by wired communication means located fully internal to the body and partially internal to the body and partially external to the body. The wired/wireless communication path that connects one or more of the implanted devices is represented by 250. One or more of the implanted devices may be configured with an internal built-in server function in addition to the intended function as an implanted medical device that performs a specified medical function. Alternately, ID5 may be configured to perform the functions of a server exclusively. The connection path 250 may be routed through the server to enable the server to exclusively communicate with devices/networks outside the body wherein the implant devices communicate with each other in conjunction with the server. Alternately, one or more of the implant devices may be enabled to communicate directly with devices/networks outside the body using one or more of the wired/wireless communication path 250, 260 and 270.

The communication path 250, 260 and 270 may utilize common communication protocols but are generally intended to be configured for communication using different wired/wireless communication protocols. The wired/wireless communication path 260 is intended to be configured for communication between one or more implanted devices/implant device network 230-IDN and one or more EPD devices EPD1, EPD2, EPD3, EPD4, EPD5, EPD6, EPD7 and EPD8 located/affixed/attached/coupled to the body of the same individual 230.

Looking now at detail of the external view of the individual 230 in FIG. 2, the figure further shows an EPD device network labeled with the legend 230-EPN, comprising of a plurality of EPD devices EPD1, EPD2, EPD3, EPD4, EPD5, EPD6, EPD7 and EPD8 that are coupled externally to the body of the same individual 230; wherein these devices are configured to communicate via wired and wireless communication means. Normally the preferred communication path between one or more of the EPD devices is intended to be a wireless communication path. However, certain selected EPD devices may be connected by wired communication means. The wired/wireless communication path that connects one or more of the EP devices is represented by 240. One or more of the EP devices may be configured with an internal built-in server function in addition to the intended function as an EP device that performs a specified medical function. Alternately, EPD5 may be configured to perform the functions of a server exclusively. The connection path 240 may be routed through the server to enable the server to exclusively communicate with devices/networks on the body wherein the EP devices communicate with each other in conjunction with the designated server EP5. Alternately, one or more of the EP devices may be enabled to communicate directly with devices/networks inside of the body using one or more of the wired/wireless communication path 240, 260 and 270.

The communication path 240, 250, 260 and 270 may utilize common communication protocols but are generally intended to be configured for communication using different wired/wireless communication protocols based on the application. The wired/wireless communication path 260 is intended to be configured for communication between one or more implanted devices/implant device network 230-IDN and one or more EPD devices/EP device network 230-EPN.

Referring to the FIG. 2 once again the individual 230 configured with a plurality of implanted devices, ID1 through ID8 located internal to the body and a plurality of electronic patch device EPD1 Through EPD8 coupled to the body is enabled for seamlessly networking with a CT/MD/MHA 284, the Internet 283, a home network/LAN/WAN 280, a office network/factory network/health care network, 281, a transportation network/public access network 282 and one or more peripheral devices comprising said networks in a secure manner while optimizing the user's criteria for power consumption, communication interference and other criteria. Additionally the system level architecture leverages the capability of an implant device to be configured to perform the functions of a server, of an electronic patch device, EPD to be configured to perform the functions of a server and of a mobile device to be configured to perform the functions of a server for enhanced communication, command and control of one or more devices within and across the various networks.

Figure 3:
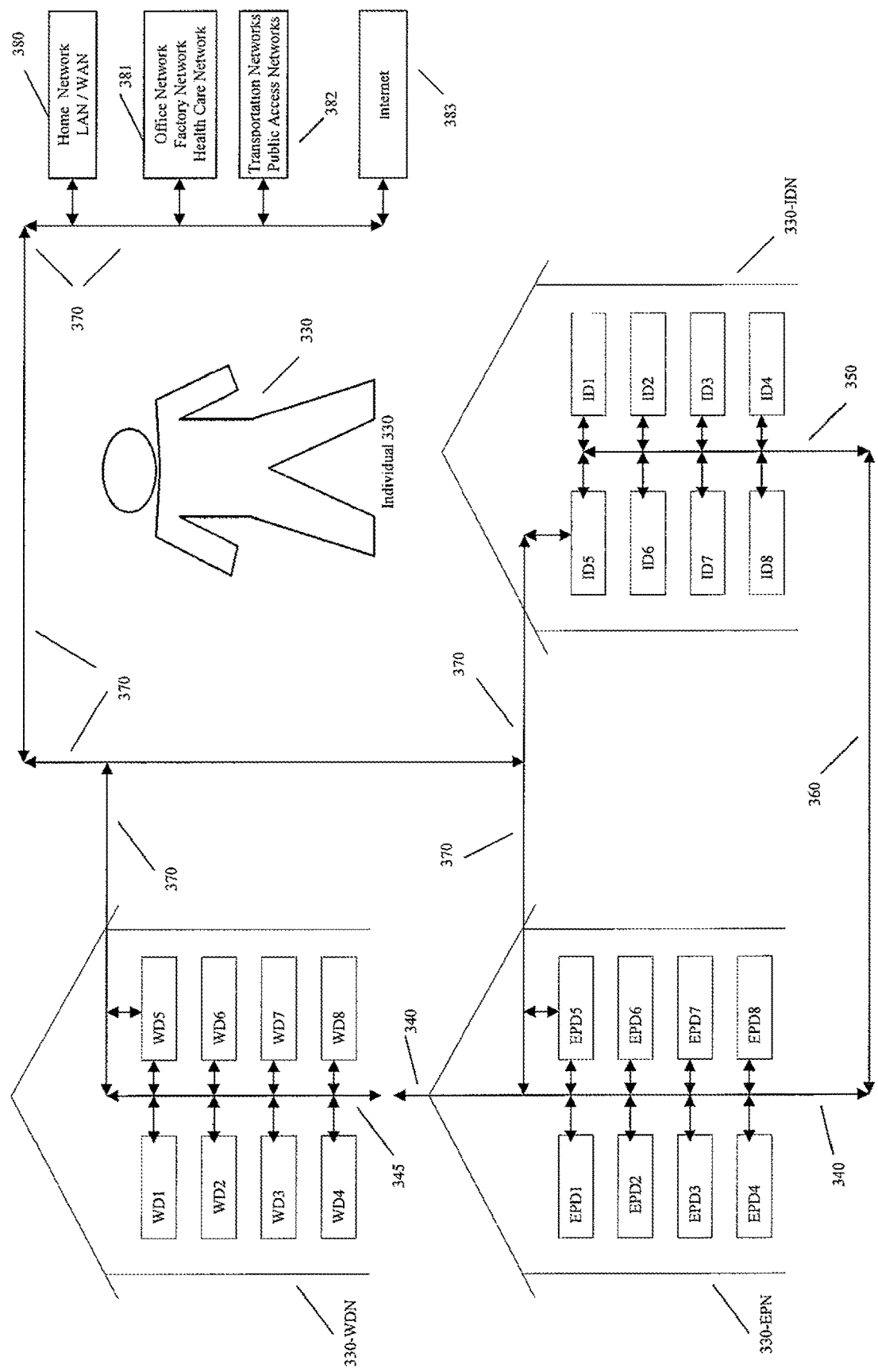
FIG. 3 shows an internal view of a body of a person/mammal with one or more implanted devices located internal to the body and the first implanted device network formed by said implanted devices.

Referring now in detail to FIG. 3, the figure shows another additional layer of a network formed by one or more wearable devices WD1, WD2, WD3, WD4, WD5, WD6, WD7 and WD8. The wearable devices may be configured for carriage within/on clothing and garments including other variations thereof that generally include a wearable device to be used as an accessory. A network formed by said wearable devices is represented by 330-WDN wherein the wearable devices such as WD1 through WD8 communicate via a wired or wireless communication path 345 internal to said wearable network 330-WDN.

The wearable devices may communicate via a wired or wireless communication path 340 for communication with one or more electronic patch devices EPD1 through EPD8 including the network 330-EPN formed by said electronic patch devices/sensors coupled to the body.

The wearable devices may further directly communicate with implanted devices ID1 through ID8 via the wired or wireless communication path 370 or indirectly via the electronic patch devices EPD1 through EPD8 via the wired or wireless communication path 360. The network formed by the implanted devices ID1 through ID8 is shown by 330-IDN. The wired or wireless communication path between the implanted devices is represented by 350.

The wearable devices WD1 through WD8 may communicate via wired or wireless communication means via the path 370 with a home network/LAN/WAN 380, an office network/factory network/healthcare network 381, a transportation network/public access network 382 and the Internet 383.

The novel system level architecture of the present invention therefore teaches a method for seamlessly networking a plurality of wearable devices with each other and further teaches the networking of one or more wearable devices worn by the individual 330, with other types of devices such as electronic patch devices coupled to the individual 330's body, implanted devices located internal to the individual 330's body, communication devices such as CT/MD/MHA that are adjacent/proximate/belong to the individual 330 and peripheral devices that are remote to the individual 330. The various wired or wireless communication paths described may utilize same or different protocols for the selected communication between selected devices forming a network or across one or more of the networks.

Additionally, the present invention teaches a novel method for configuring a wearable device such as WD5 to solely serve the functions of a server to enable the network 330-WDN to perform efficiently or in a selected manner. Alternately one or more of the wearable devices WD1 through WD8 may additionally be configured with the functionality of a server in addition to any other desired functionality. The wearable devices WD1 through WD8 may be configured to perform one or more selected functions such as measuring/monitoring temperature, wind velocity and other environmental parameters and may also be configured to sense/measure/monitor bodily parameters related to the individual 330. The present invention enables the seamless correlation of one or more environmental parameters, parameters on the surface of the body and parameters internal to the body thus enhancing the ability of the individual 330 to control the selected parameters internal or external to the body in response to a sensed, measured or monitored value in real time.

For example the presence of extreme cold temperatures in the environment may be sensed by a wearable sensor WD1 and communicated to the wearable device WD5 that serves the server function such that the wearable devices WD2, WD3, WD4, WD6, WD7 and WD8 located at different regions of a garment may regulate the temperature of the garment/clothing in a manner selected by the individual for a desired comfort level at various anatomical locations of the body. As an example the heat may be provided to selected location within the garment/clothing by a heating mechanism that is powered by battery. The regulation of the temperature may be done in conjunction with the sensed body temperature at the surface of the body via one or more of the electronic patch devices EP1 through EP8 that are coupled to the body. The wearable sensor device WD5 performing the functions of a server in the wearable sensor/device network 330-WDN may coordinate with the electronic patch device EPD5 performing the functions of a server in the 330 EPN network. Similarly the WD5 and EPD5 may coordinate with one or more implant devices such as the ID5 performing the functions of a server in the 330-IDN network to regulate/command/control the functions of one or more implant devices located internal to the body. The present invention therefore teaches a seamless method for communication/regulation/command and control of human/mammalian body parameters internal to said body and at said body in response to environmental and other factors sensed/measured/monitored through wearable sensors worn by an individual in one or more forms including in clothing and garments. For example, pacing of the heart may be controlled in a desired manner in response to a measured value of one or more parameters such as temperature, altitude, ambient pressure of the environment as measured by a wearable sensor device WD1, a value of temperature and electro cardiogram information as measured by an electronic patch sensor device EPD1 such that a pacemaker implanted device ID1 regulates the pacing in accordance with a selected pacing protocol as determined by the individual 330 or a remote physician/health care professional via wired or wireless communication.

Often the physician requires more than one parameter to be sensed and measured for recommending the best course of action for an individual patient. Therefore there is a need for locating a plurality of sensor devices within the body, on the body or within wearable clothing to sense each parameter in a dedicated manner. However, the need for multiple sensors/devices each performing a single function may be obviated by configuring a single sensor/device that performs multiple functions within said unit.

Figure 4:
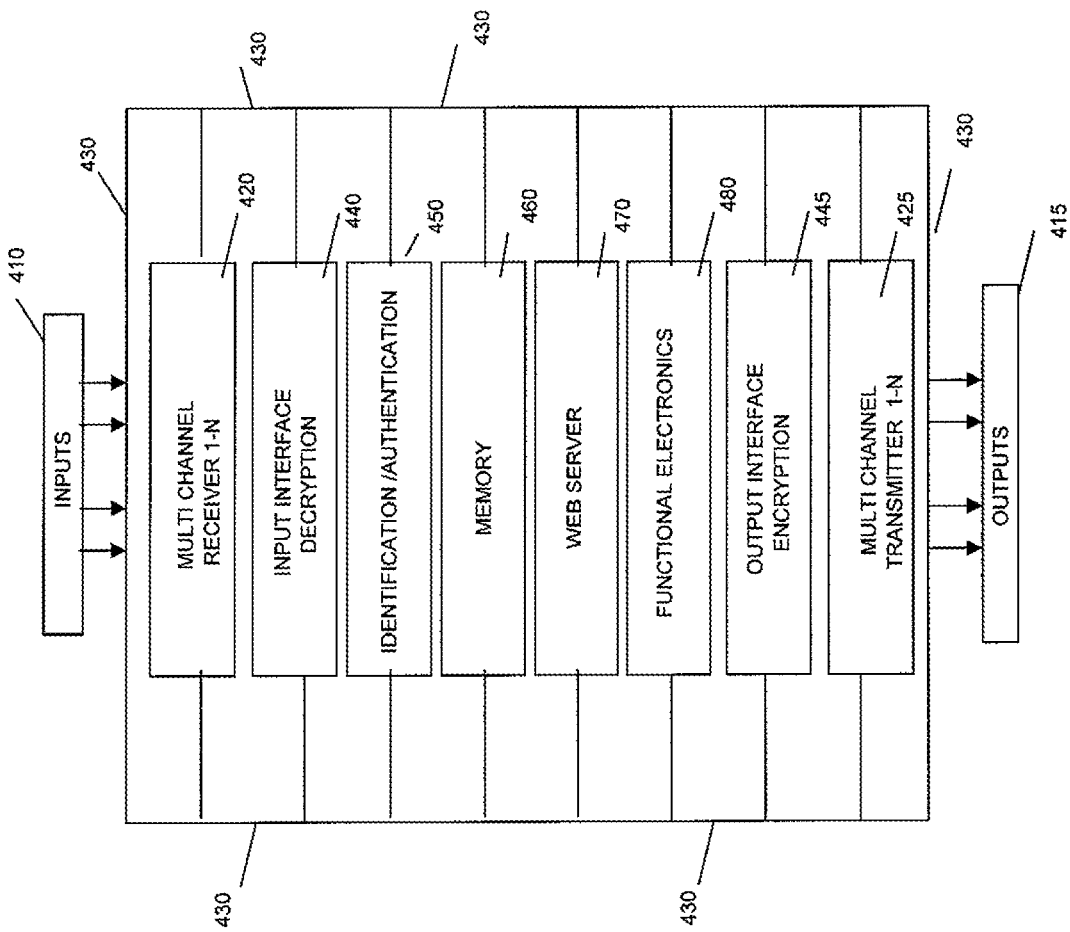
FIG. 4 additionally shows another third network formed by one or more wearable devices configured for carriage on the body.

Referring now to FIG. 4 in detail, a sensor device 430 configured with a plurality of inputs 410, a plurality of outputs 415, a multi-channel receiver 420, a multi-channel transmitter 425, an input interface and decryption functional block represented by 440, an identification and authentication functional block represented by 450, a memory functional block represented by 460, a web server/server functional block represented by 470, other functional electronics/ sensing/measuring mechanism represented by 480 and an output interface and encryption functional block represented by 445 is shown. The figure is for illustration purposes and other configurations and organization of the various functional blocks is possible by those knowledgeable in the art and the illustration is not to be construed as limiting.

The illustration of the FIG. 4 is generally applicable for wearable devices WD1 through WD8; for electronic patch/ sensor devices that are coupled to the body EPD1 through EPD8 and for implantable devices ID1 through ID8. Consequently only one figure is shown and is intended to cover the various types of sensors and devices as referred to herein. The present invention described the need for a sensor device/medical to communicate utilizing one or more communication protocols to communicate across the different networks such as 330-WDN, 330-EPN, 330-IDN as shown in FIG. 3 and with a host of proximate and remote devices such as CT/MD/MHA 190 and a remote central server as shown in FIG. 1. In order for a wearable device WD1, an electronic patch device EPD1 and an implantable device ID1 to communicate within its own network and outside of its own network, it would be desirable for each of said devices to have multi-channel communication capabilities that are appropriate for a selected communication with a selected device within a network and outside of said network. The present invention teaches wearable devices, electronic sensor devices and implantable devices that have multi-channel communication capabilities using one or more communication protocols. For example, the use of the appropriate protocol by an implantable device conserves power, minimizes interference and enhances security.

Figure 5:
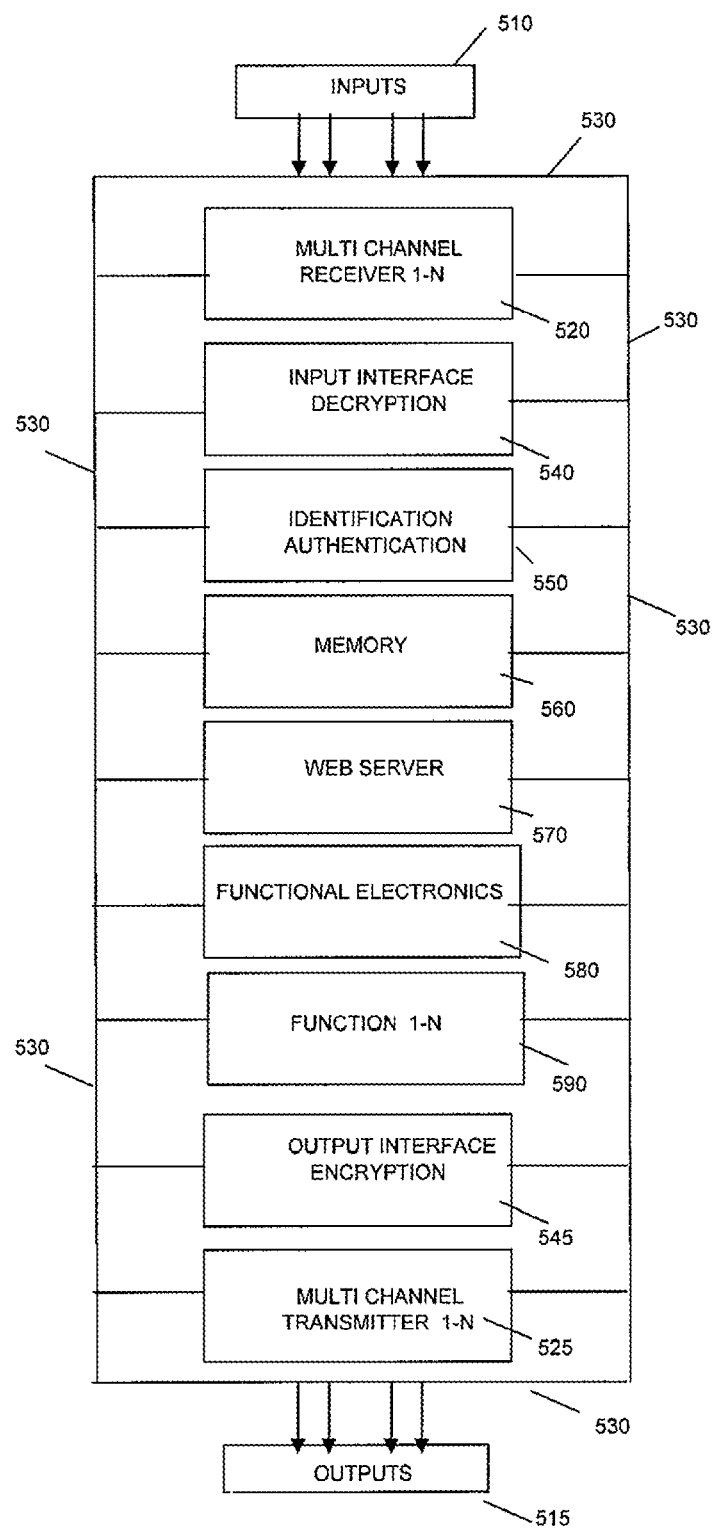
FIG. 5 shows an illustrative functional block diagram configuration of a multifunction implantable device; a multifunction electronic patch/electro-physiological/biological sensor device that may be located on, affixed to or coupled to the body; and a multifunction wearable device for carriage on the body wherein the illustrated block diagram of these different devices shows a plurality of functionalities 1 through N for use in conjunction with one or more input and output channels that are configured for one or more of dedicated and multiplexed wired and wireless communication. The block diagram configuration shown is for illustrative purposes and is not intended to be limiting in any way as to the presence of one or more of the functional blocks and the exclusion of one or more of the functional blocks. As an example other functions that are not illustrated may be included/excluded by those knowledgeable in the art for configuring a selected multifunction device based on the desired application needs.

Referring now to FIG. 5, a multi function device configuration 530 is illustrated and is generally intended to cover implantable devices ID1, electronic patch/sensor devices EPD1, and wearable devices WD1. The figure shows a functional block 510 comprising of a plurality of inputs, a functional block 515 comprising of a plurality of outputs, a multi channel receiver block 520, a multi channel transmitter block 525, an input interface/decryption block 540, an identification/authentication block 550, a memory block 560 wherein the memory may be of different types; a server/web server functional block 570, a functional electronics block 580, a function block 590 wherein one or more functions may be configured/selected and actuated to sense, measure and monitor one or more selected parameters and perform one or more functions; and an output interface/ encryption functional block 545.

Referring now to FIG. 5, in addition to multi-channel communication capability, there is a need for one single device such as an implantable device to perform more than one function. For example, an implanted pace maker device that measures cardiac activity and controls cardiac function may be enhanced if the same device additionally performs blood flow measurements within the artery, blood oxygen levels and even temperature at a given location in the veins. The combination of functions saves space, eliminates the need for multiple devices and the surgical procedures for implanting a plethora of devices and provides a method for obtaining a more comprehensive set of information needed by the physician to better treat the patient and to correlate specific information to prior history of the patient and the population at large. The present invention teaches a multi function implantable device ID1, a multi function electronic patch device EPD1, a multi function wearable device WD1 wherein each said device has the capability to communicate on one or more channels utilizing a plurality of communication protocols that are appropriate for a selected communication between one or more devices and across one or more networks comprising of said devices.

There is also a need for generally or selectively utilizing encryption and decryption in the selected communications to maintain security and data integrity to ensure that vital statistics and information is not easily accessible by unauthorized individuals. The present invention couples various types of authentication including biometric authentication such as hand writing, speech/voice recognition, photo, image, finger print, retinal scan and other methods to grant or deny access to a particular device such as ID1, EPD1, WD1 and other peripheral devices and one or more networks comprising said devices to enhance individual/patient safety and security including limiting accidental or spurious access that could be potentially damaging or life limiting.

Referring now to FIG. 6, the figure illustrates a matrix for dynamic configuration of new functional networks, 600 comprising defined networks, 601 and defined devices 602. FIG. 6 further comprises of an implant device network 603 comprising of a plurality of implant devices ID1 through ID8, 604; an electronic patch/sensor device network 605 comprising of a plurality of electronic patch/sensor devices EPD1 through EPD8, 606; a wearable device network 607 comprising of a plurality of wearable devices WD1 through WD8, 608; and a LAN/WAN/Internet/home network/office network/health care facility network/transportation network/ public access network and other networks 609 comprising of a plurality of peripheral devices such as CT/MD/HMA, PHMA, PC/TV, servers, printers and other remote equipment represented by 610.

Referring to FIG. 6 in detail for example a new network comprising of an implant device ID3 and ID4; EPD1 and EPD6 and a wearable device WD2 may be dynamically configured to sense, measure and manage a desired set of parameters to control a desired set of biological parameters related to an individual. The communication across these selected devices may utilize one or more selected communication protocols.

Referring once again to FIG. 6 in detail for example another new network comprising of an implant device ID3 such as pace maker; EPD1 such as a device that measures body temperature, EPD3, EPD4, EPD6, EPD7 and EPD8 that measure cardiac function and EPD5 which serves as a server and a wearable device WD2 that measures ambient temperature and altitude may be dynamically configured to sense, measure and manage a desired set of parameters to control a desired set of biological parameters related to an individual. The communication across these selected devices may utilize one or more selected communication protocols. The dynamically configurable biological sensor/ device networks may comprise of multi channel and multi function devices wherein a single device that performs multiple functions may be configured to be part of a plurality of dynamically configured networks. As an example a multi function device ID1, EPD1, WD1 wherein one function is that of sensing/measuring temperature may be configured to be part of a temperature sensing/control network, a first network wherein said first network utilizes a first communication protocol for communication on a first input/output channel of said respective devices; and wherein the same devices ID1, EPD1 and WD1 measuring cardiac function may be part of a second dynamically configured network wherein the second network utilizes a first communication protocol or a second communication protocol for communication on a first or second input/output channel of said respective devices. Therefore the present invention teaches novel ways to partition the selected functionality of a multi function device and enables the dynamic configuration of multi function sensors and devices around either the selected functionality, the selected communication protocols or other attributes and combinations of said devices for dynamic utility. The present invention teaches novel devices located internal/on the body/external to the body wherein said devices may be configured to form a plurality of wired and wireless networks for the acquisition, processing, computation, storage and communication of information. The system of the present invention further enables the command and control of said individual devices and the plurality of networks comprising of said devices.

The embodiments herein include a system and method for dynamically configuring implantable medical devices to form an implantable device network.

The embodiments herein include a system and method for dynamically configuring electronic patch sensor devices that are coupled to the body to form an electronic patch sensor device network.

The embodiments herein include a system and method for dynamically configuring wearable devices to form a wearable device network wherein the wearable devices are worn on the body.

The embodiments herein include a system and method for dynamically configuring a network of implantable devices, electronic patch sensor devices and wearable devices to form a layered network for seamless and continuous monitoring of human body parameters.

The embodiments herein include a system and method for dynamically configuring a network of implantable devices, electronic patch sensor devices, wearable devices and remote devices to form a layered network for seamless monitoring of human body parameters including the communication of one or more human body parameters to a remote device/network for measurement, monitoring, archival and for command and control.

The embodiments herein include a system wherein the individual device/sensor is uniquely addressable for safe, secure and intended communication with a selected level of device/user authentication including biometric authentication.

The embodiments herein include a system wherein a network formed by selected devices/sensors is uniquely addressable for safe, secure and intended communication with a selected level of device/user authentication including biometric authentication.

The embodiments herein include a system for dynamically forming one or more new networks by selecting one or more individual/groups of devices/sensors from one or more other defined networks wherein the new network is configured for a defined functional task and/or a defined utility at a selected time and for a selected duration.

Aspects of the embodiments described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the embodiments include: microcontrollers with memory (such as electronically erasable programmable read only memory (EEPROM)), embedded microprocessors, firmware, software, etc. Furthermore, aspects of the embodiments may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments is not intended to be exhaustive or to limit the systems and methods to the precise forms disclosed. While specific embodiments and examples are described herein for illustrative purposes, various equivalent modifications are possible within the scope of the systems and methods, as those skilled in the relevant art will recognize. The teachings of the embodiments provided herein can be applied to other systems and methods, not only for the systems and methods described above.

The elements and acts of the various embodiments described above can be combined to provide further embodiments. These and other changes can be made to the embodiments in light of the above detailed description.

In general, in the following claims, the terms used should not be construed to limit the embodiments to the specific embodiments disclosed in the specification and the claims, but should be construed to include all systems that operate under the claims. Accordingly, the embodiments are not limited by the disclosure, but instead the scope of the embodiments is to be determined entirely by the claims.

While certain aspects of the embodiments are presented below in certain claim forms, the inventors contemplate the various aspects of the embodiments in any number of claim forms. Accordingly, the inventors reserve the right to add additional claims after filing the application to pursue such additional claim forms for other aspects of the embodiments.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A system including a mobile device and a wearable device, said system comprising:
    a medical device configured for placement within a body, wherein the medical device further comprises a processor;
    a monitoring system comprising of: an internal health data recorded by the medical device and received by the wearable device via a first wireless connection; wherein the wearable device is enabled to receive the internal health data periodically and/or continuously;
    wherein the wearable device is enabled to be in contact with the surface of the body; wherein the wearable device is further configured to acquire a physical activity data of the body;
    wherein the wearable device is configured to measure one or more environmental parameters; wherein at least one configuration of the medical device is controlled in response to the measured one or more environmental parameters;
    wherein the mobile device is enabled to receive from the wearable device via a second secure wireless network connection the physical activity data and the internal health data; wherein the mobile device is enabled to send to a server the physical activity data and the internal health data;
    the server enabled for archival of the physical activity data and the internal health data; wherein the physical activity data and the internal health data is enabled for remote access; and
    wherein the server is enabled to correlate the physical activity data with the internal health data.

2. The system of claim 1, further comprising the wearable device comprising: a sensor, a battery, and a processor; wherein the wearable device is enabled to measure a plurality of signals.

3. The system of claim 2, wherein the wearable device is a multifunction wearable device further comprising the functions of capturing an electrocardiogram (ECG) signal.

4. The system of claim 1, wherein the medical device is a defibrillator.

5. The system of claim 1, wherein the medical device is a pacemaker configured for control via remote access in response to the one or more environmental parameters.

6. The system of claim 5, wherein a communication network is formed between the wearable device and the mobile device; and wherein the wearable device is communicatively in communication with the mobile device and further in communication with the medical device.

7. The system of claim 6, further comprising a non-transitory computer readable medium to be executed by a processor on the mobile device in the form of a mobile application to manage and control the wearable device.

8. A system including a mobile device, said system comprising:
    a wireless device, comprising a processor and a wireless transmit and receive unit; wherein the wireless device is enabled to acquire a physical activity health data;
    a medical device comprising a processor;
    wherein the medical device is in communication with the wireless device;
    wherein the medical device is enabled to acquire an internal health data;
    wherein the medical device is enabled to send via a first secure wireless connection the internal health data to the wireless device;
    wherein the wireless device is a wearable device; wherein the wearable device is configured to measure one or more environmental parameters;
    wherein the wearable device is enabled to capture an electrocardiogram;
    the mobile device enabled to receive from the wireless device via a network connection the physical activity health data and the internal health data;
    wherein the mobile device is enabled to send the physical activity data and internal health data to a server;
    wherein the server is enabled to correlate the physical health data with the internal health data; and
    wherein the server and/or mobile device analyzes, to determine at least one trend, one or more of the one or more environmental parameters, the electrocardiogram, the internal health data, and the physical activity data.

9. The system of claim 8, wherein the medical device is configured to communicate with a wearable device with a first wireless communication protocol; and wherein the wearable device is enabled to communicate to the wireless device using a second wireless protocol.

10. The system of claim 9, wherein the networking between the medical device and a wearable device comprises of a hierarchical communication architecture such that the medical device is enabled for communication at a one or more channels.

11. The system of claim 10, wherein networking is enabled for routing of information based on power levels.

12. The system of claim 8, further comprising a non-transitory computer readable medium to be executed by a processor on the mobile device in the form of a mobile application to manage and control the medical device.

13. The system of claim 12, wherein the medical device is a heart pacemaker.

14. The system of claim 8, wherein the medical device is an implantable device enabled for wireless communication to a wearable device and control by the wearable device.

15. The system of claim 14, wherein the medical device is a defibrillator.

16. The system of claim 15, further comprising a remote server configured to record health data obtained from the medical device.

* * * * *